United States Patent [19]
Pardey et al.

[11] Patent Number: 5,999,846
[45] Date of Patent: Dec. 7, 1999

[54] PHYSIOLOGICAL MONITORING

[75] Inventors: James Pardey; Mark Jeremy Laister, both of Oxford; Michael Richard Dadswell, Oxon; Lionel Tarassenko, Oxford, all of United Kingdom

[73] Assignee: Oxford Medical Limited, Oxon, United Kingdom

[21] Appl. No.: 08/745,780

[22] Filed: Nov. 8, 1996

[30] Foreign Application Priority Data

Nov. 8, 1995 [GB] United Kingdom .................... 9522872

[51] Int. Cl.$^6$ .................................................. A61B 5/04
[52] U.S. Cl. ........................................................ 600/544
[58] Field of Search .................................. 600/509, 513, 600/544, 555, 546, 545

[56] References Cited

U.S. PATENT DOCUMENTS

| | | |
|---|---|---|
| 4,776,345 | 10/1988 | Cohen et al. |
| 5,047,930 | 9/1991 | Martens et al. ........................... 600/544 |
| 5,222,503 | 6/1993 | Ives et al. ................................ 600/544 |
| 5,299,118 | 3/1994 | Martens et al. ........................... 600/544 |
| 5,447,166 | 9/1995 | Gevins et al. ............................ 600/544 |
| 5,450,855 | 9/1995 | Rosenfeld ................................. 600/545 |

OTHER PUBLICATIONS

S. Roberts et al., *New Method of Automated Sleep Quantification,* Medical & Biological Engineering & Computing, Sep. 30, 1992.

Robert G. Norman, et al., *A Likelihood Based Computer Approach to Conventional Scoring of Sleep,* Proceeding of the Annual International Conference of the IEEE Engineering in Medical and Biology Society, Oct. 29—Nov. 1, 1992.

Gregory Belenky, et al., *Discrimination of Rested From Sleep–Deprived EEG in Awake Normal Humans by Artificial Neural Network,* IEEE, 1994.

*Primary Examiner*—Robert L. Nasser
*Attorney, Agent, or Firm*—Hoffmann & Baron, LLP

[57] ABSTRACT

An insomnia or vigilance monitor comprising one or more electrodes (1$a$,1$b$) for obtaining an electrical signal from a subject over a period of epochs, the electrical signal being related to the sleep or wakefulness stage type being experienced by the subject; and a processor (5) adapted to analyze the electrical signal and assign a sleep or wakefulness stage type to each epoch to generate a hypnogram. Methods of monitoring sleep or vigilance using the mastoid site are also disclosed. Further disclosures relate to a method of training and testing a first neural network for use in a physiological monitor, and a method of assigning a class to an epoch of a physiological signal obtained from a subject as a set of samples.

13 Claims, 11 Drawing Sheets

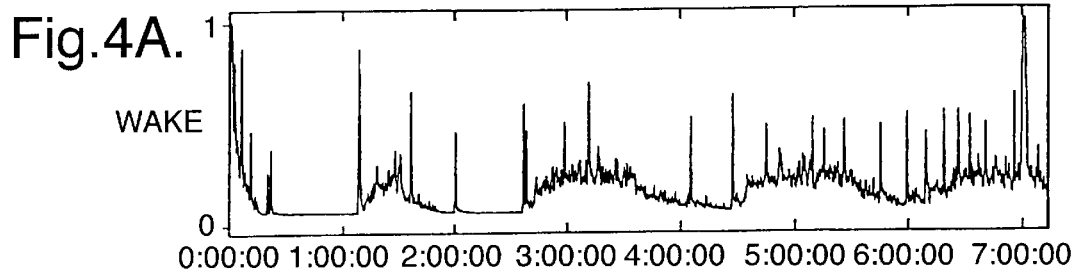
Fig.4A. WAKE
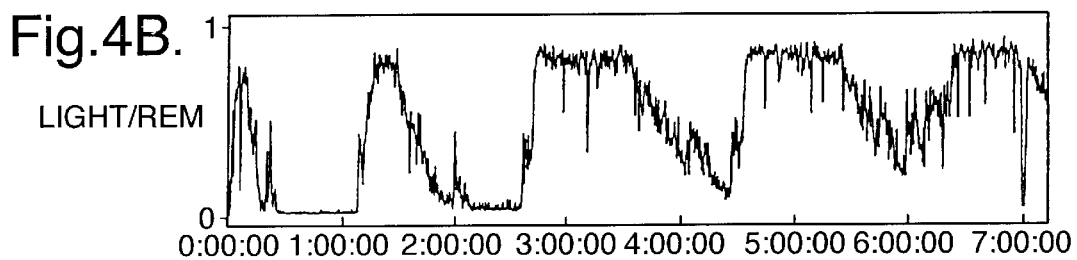
Fig.4B. LIGHT/REM
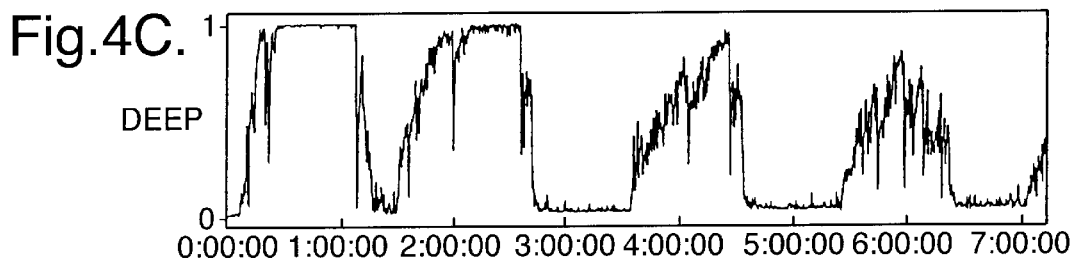
Fig.4C. DEEP
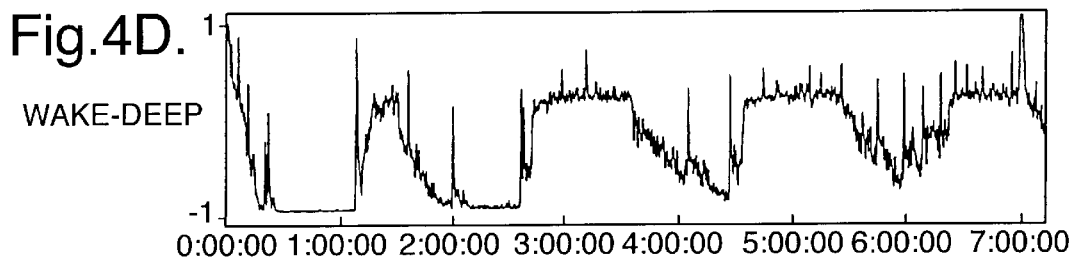
Fig.4D. WAKE-DEEP
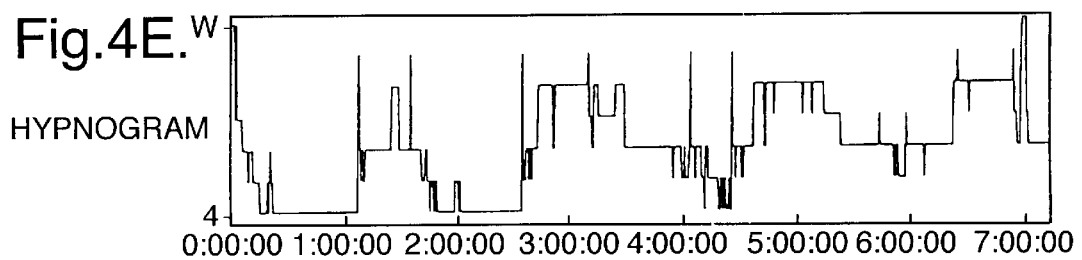
Fig.4E. HYPNOGRAM

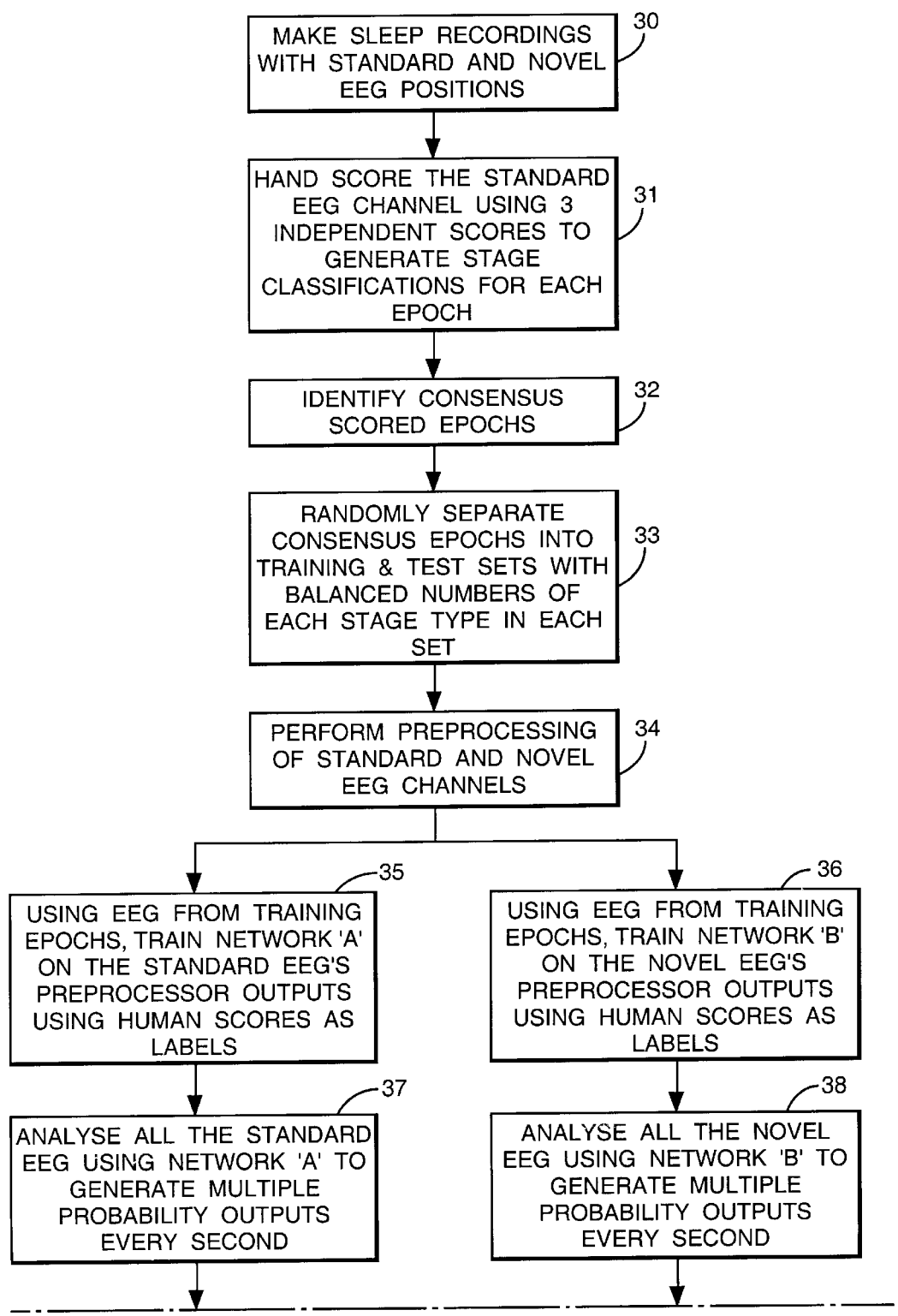

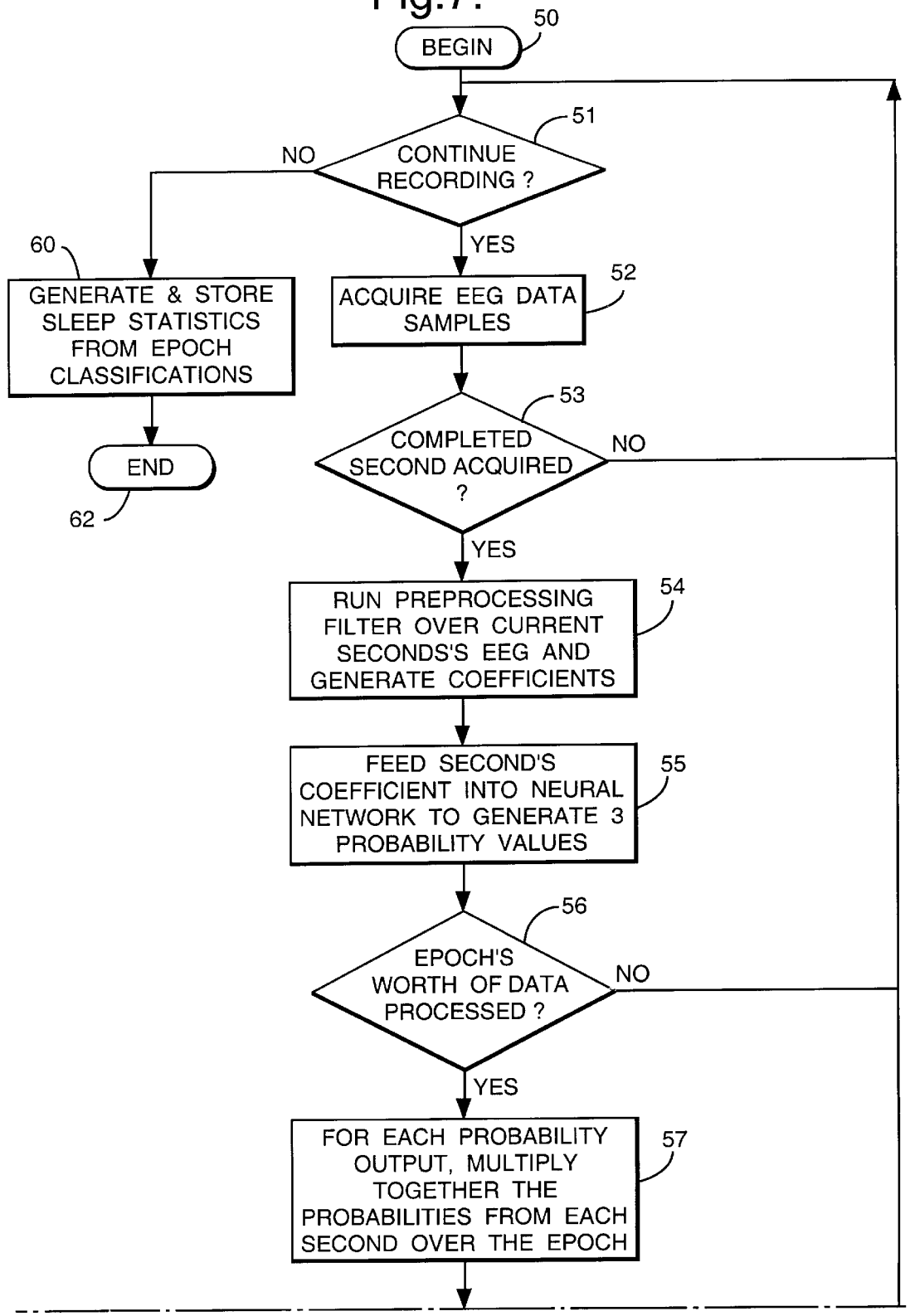

Fig. 8A. CENTRAL EEG: WAKE
```
x . . . . . . . . .
. . . . . . . . . .
. . . . . . . . . .
. . . . . . . . . .
. . . . . . . . . .
. . . . . . . . . .
x . . . . . . x x .
x x x . . . . x x x
x x x x x . x x x x
x x x x x x x x x x
```

Fig. 8B. CENTRAL EEG: REM
```
. . . . . . . . . .
. . . . . . . . . .
. . . . . . . . . .
x . . . . . . . . .
x x . . . x . . . .
x x x x x x x . . .
x x x x x x x . x .
. x x x x x x x . .
. . x x x x . . . .
. . . . . . . . . .
```

Fig. 8C. CENTRAL EEG: SWS
```
. . x x x x x x . .
. x x x x x x x . .
x x x x x x . . . .
. . . x x . . . . .
. . . . . . . . . .
. . . . . . . . . .
. . . . . . . . . .
. . . . . . . . . .
. . . . . . . . . .
. . . . . . . . . .
```

Fig. 8D. CENTRAL EEG: STAGE 1
```
. . . . . . . x x x
. . . . . . . x x x
. . . . . . . x x x
x x x x . . x x x x
. x x x x x x x x x
x x . . . x x x x x
. . . . . . . x . .
. . . . . . . . . .
. . . . . . . . . .
. . . . . . x . . .
```

Fig. 8E. MASTOID EEG: WAKE
```
x x x x x x x x . .
x x x x x . . . . .
x x x . . . . . . .
x x . . . x . . . .
. . . . . . . . . .
x . . . . . . . . .
x x . . . . . . . .
x x x . . . . . . .
x x . x . . . . . .
x x x x x . . . . .
```

Fig. 8F. MASTOID EEG: REM
```
. . . . x x x . . .
. . . . x x x x . .
. . x x x x x . . .
. x x x x x x . . .
. . . x x x . . . .
x x x x x . . . . .
. x x x x . . . . .
. x x x x . . . . .
. . x x x . . . . .
. . . . x x . . . .
```

Fig. 8G. MASTOID EEG: SWS
```
. . . . . . . . . .
. . . . . . . . . .
. . . . . . . . . .
. . . . . . . . x x
. . . . . . . x x x
. . . . . . . x x x
. . . . . . . x x x
. . . . . . . . x x x
. . . . . . . . x x x
. . . . . . . . . x x
```

Fig. 8H. MASTOID EEG: STAGE 2
```
. . . . . . x x x x
. . . . . x x x x x
. . . . x x x x x x
x . x x x . . . . .
x x x x . . . . . .
x x x x . x . . . .
. . . . . x . . . .
. . . x x x . . . .
. . x x x x x x . .
. . . . . x x x . .
```

AWAKE

ALPHA ACTIVITY    BETA ACTIVITY

STAGE 1 SLEEP

THETA ACTIVITY

STAGE 2 SLEEP    K COMPLEX

SPINDLE

STAGE 3 SLEEP

SECONDS
0 1 2 3 4 5

DELTA ACTIVITY

STAGE 4 SLEEP

DELTA ACTIVITY

REM SLEEP

THETA ACTIVITY    BETA ACTIVITY

PHYSIOLOGICAL MONITORING

FIELD OF THE INVENTION

The present invention relates to improvements in physiological monitoring, in particular sleep or vigilance monitoring.

DESCRIPTION OF THE PRIOR ART

The method currently employed world-wide for scoring sleep recordings is described in Rechtschaffen and Kales (1968), "A Manual of Standardized Technology, Techniques and Scoring System for Sleep Stages of Human Subjects".

Scoring requires the following signals to be recorded;

electroencephalogram (EEG)—from a position near the top of the head, two eye channels (electro-oculogram (EOG))—from electrodes near the outer canthus of each eye, and chin muscle tone (electromyogram (EMG))—from a pair of electrodes under the chin.

Sleep scoring breaks the recording into epochs of typically 20, 30 or 40 seconds duration. Each epoch has a sleep stage classification applied to it. The six recognised classifications are: Stage Wake; Stage REM (Rapid Eye Movement); Stages 1, 2, 3 and 4. The classification of each epoch first requires the identification of particular features in the EEG and EOG, and measurement of the amplitude of the EMG relative to the background EMG level. The features are identified using frequency and amplitude criteria. Such a recording technique and method of scoring is known as polysomnography.

A set of rules is then applied to the features to obtain the classification for each epoch.

Examples of conventional EEG traces which have been assigned to the sleep stages mentioned above are shown in FIGS. 9(a)–(f). FIGS. 9(a)–(f) show the following stages;

FIG. 9(a)-awake;

FIG. 9(b)-stage 1;

FIG. 9(c)-stage 2;

FIG. 9(d)-stage 3;

FIG. 9(e)-stage 4;

FIG. 9(f)-REM.

Once each epoch has been assigned a classification cleanup rules are applied that can reclassify certain epochs according to their context.

The classifications of each epoch for the entire night's recording can be plotted against time. This is a hypnogram.

Summary statistics can be derived from the hypnogram that allow objective measures of the quality of sleep to be made.

SUMMARY OF THE INVENTION

According to a first aspect of the present invention there is provided an insomnia monitor comprising (1) one or more electrodes for obtaining an electrical signal from a subject over a period of epochs, the electrical signal being related to the sleep stage type being experienced by the subject;

(2) a processor adapted to analyze the electrical signal and assign a sleep stage type to each epoch to generate a hypnogram;

(3) means for analysing the hypnogram to generate a summary index of sleep quality over the period of epochs; and (4) means responsive to the means for analysing the hypnogram to display the summary index of sleep quality.

The present invention provides a device which can be self contained, portable and cheap. The device generates and displays a summary index which provides a simple objective indicator of the degree of insomnia suffered by the subject.

Insomnia can manifest itself in many forms, and therefore different sleep summary indices may be generated and displayed. For instance a subject may experience a simple lack of sleep. In this case a low Sleep Efficiency Index (which is the ratio of the time asleep to the time in bed) will provide the required indication and is generated and displayed. Alternatively the subject may have a high Sleep Efficiency Index but may sleep "badly". For instance the subject may experience irregular sleep cycles (eg alternating long/short periods of REM sleep). Therefore an alternative or additional summary index may comprise an indication of the periodicity of the sleep/wake continuum. For instance the index may be derived from the periodicity, variance of frequency etc. of one or more categories of sleep.

Typically the device is worn by a subject during the night, during which time it continually acquires and analyses the electrical signal which is typically an EEG signal from the subject's scalp. When the recording is terminated in the morning it provides one or more simple indices of sleep quality which indicate how well the subject slept. Values below predetermined thresholds indicate that the subject should refer to either a general practitioner or a sleep laboratory for further investigation.

The device is primarily intended for use by general practitioners for use as a screening tool for subjects who claim to be insomniacs and for members of the public who wish to monitor the quality of their own sleep.

Providing a summary index reduces the time taken by the physician to make a decision on whether additional treatment is required, and it does not need particular skills, making it more suitable for GPs to use. Preferably the summary index comprises a Yes/No value indicating whether or not the subject suffers from some form of insomnia.

The first aspect of the present invention also extends to a method of sleep monitoring, the method comprising:

(1) obtaining an electrical signal from a subject over a period of epochs, the electrical signal being related to the sleep stage type being experienced by the subject;

(2) analysing the electrical signal and assigning a sleep stage type to each epoch to generate a hypnogram;

(3) analysing the hypnogram to generate a summary index of sleep quality over the period of epochs; and (4) displaying the summary index of sleep quality.

Using the same physiological parameters and using a similar process to that described above but employing an alternative set of rules to those of Rechtschaffen and Kales it is possible to construct a "Wakeogram" that indicates the degree of wakefulness of the subject before they fall asleep, as well as their depth of sleep once they are asleep. From the Wakeogram it is possible to derive a measure of the vigilance of the subject.

In accordance with a second aspect of the present invention there is provided a vigilance monitor comprising (1) one or more electrodes for obtaining an electrical signal from a subject over a period of epochs, the electrical signal being related to the wakefulness stage type being experienced by the subject;

(2) a processor adapted to analyze the electrical signal and assign a wakefulness stage type to each epoch to generate a Wakeogram;

(3) means for monitoring the output of the Wakeogram to determine whether the output of the Wakeogram meets predetermined criteria; and (4) means responsive to the means for monitoring the Wakeogram to generate a message when the output of the Wakeogram meets the predetermined criteria.

The second aspect of the invention provides a vigilance monitor which allows people in safety-critical jobs to have their vigilance directly monitored. Vigilance analysis requires segmentation and classification of the electrical signal during wakefulness as well as during sleep. A suitable scoring technique classifies wakefulness into several different categories, each representing a lower state of alertness or vigilance. The scorers may use an arbitrary epoch length of typically 20 seconds, but other epochs could be chosen (as per sleep). Just as for sleep, scoring is based on visual methods.

The electrical signal or Wakeogram may be stored for later analysis or monitoring. In this case the electrical signal or Wakeogram may be analysed at a later date to determine whether a predetermined level of vigilance has been maintained over the period of epochs. In this case the vigilance monitor typically comprises means for analysing the Wakeogram to generate a summary index of vigilance quality over the period of epochs. The summary index may be stored for later output, or may be displayed by the vigilance monitor. Preferably however the Wakeogram is analysed and the message is generated during the period of epochs. In this case, the message gives a real-time continuous indication of the vigilance of the subject.

When the output of the Wakeogram meets the predetermined criteria, which typically have been determined in advance as representing a lowered level of vigilance, the device generates a message of some kind. This might be an audible, visual or electronic message and may be used to alarm the subject.

The second aspect of the present invention also extends to a method of vigilance monitoring, the method comprising:

(1) obtaining an electrical signal from a subject over a period of epochs, the electrical signal being related to the wakefulness stage type being experienced by the subject;

(2) analysing the electrical signal and assigning a wakefulness stage type to each epoch to generate a Wakeogram;

(3) monitoring the Wakeogram to determine whether the output of the Wakeogram meets predetermined criteria; and (4) generating a message when the output of the Wakeogram meets the predetermined criteria.

The following comments apply both to the insomnia monitor according to the first aspect of the present invention and to the vigilance monitor according to the second aspect of the present invention.

The hypnogram or Wakeogram may be generated from a plurality of electrical signals from standard sites (eg EEG, EOG, EMG etc). Preferably however the device generates the hypnogram or Wakeogram from a single channel only (preferably an EEG channel). The use of only a single EEG channel reduces the cost of amplification circuitry, and fewer electrodes are required to perform a recording than traditional polysomnography recordings.

The device typically comprises a portable, battery powered, self contained unit.

The summary index or message is typically generated within the device. The index or message can then be represented by displaying it on a digital display and/or by sounding an audible alarm and/or by storing it within the device for later review. Alternatively the index or message may be transmitted to another device (e.g. by transmitting it to a computer via a serial interface).

The insomnia or vigilance monitor may store the original EEG signal and analyze the stored signal at the end of a period of sleep or at the end of a period of vigilance monitoring. Typically however the insomnia monitor or vigilance generates the hypnogram or Wakeogram "on-the-fly" and further comprises a memory adapted to store the hypnogram or Wakeogram. This minimises the cost of memory—12 hours of EEG would require typically 4MB of non-volatile storage. If the analysis is performed on-line only the results need to be stored, which can be done more cheaply, in a few kB.

According to a third aspect of the invention there is provided a method of sleep or vigilance monitoring, the method comprising obtaining an EEG signal from the mastoid site behind a subject's ear, and performing sleep or vigilance analysis on the EEG signal.

The mastoid site provides a novel site for monitoring electrical activity to monitor sleep or vigilance quality. The mastoid sites lie below the hairline. This allows disposable, stick-on electrodes to be used instead of the glued-on electrodes normally required for sleep studies. The latter require acetone based glues and solvents to be used, and require trained personnel to fit them.

The mastoid signal cannot necessarily be interpreted by humans but offers advantages in terms of hook-up time, convenience, comfort, aesthetics, and lowered skill requirements for application.

Typically the method comprises obtaining a differential signal between the two mastoid sites.

Preferably the sleep or vigilance analysis (such as polysomnography analysis) is carried out on the mastoid EEG signal alone. Typically the analysis is carried out by a neural network.

Preferably the first and/or second and third aspects of the invention are combined, ie. the electrical signal is obtained in step (1) from the mastoid site.

The sleep-wake continuum can be fully described in terms of a finite number of continuous processes; for insomnia monitoring these are Wakefulness, Dreaming/Light Sleep and Deep Sleep. These correspond to the human-scored stages of Wake, REM/Stage 1 and Stage 4. Wakefulness can be further partitioned into different degrees of Wakefulness or Vigilance, such as Active Wake, Quiet Wake, Wake with high alpha content, Wake with high theta content. What is required is a means of tracking the time course of the EEG as it moves between these processes.

Typically the processor of the first or second aspect of the invention and the means for performing sleep or vigilance analysis according to the third aspect of the invention comprises a neural network such as a multilayer perceptron (MLP). The requirements outlined above are ideally matched to the functional capabilities of an MLP. This neural network can be trained to perform polysomnography analysis on a single EEG channel (instead of 1 EEG, 2 EOG and 1 EMG). It also can be trained to analyze an unconventional EEG signal, such as the mastoid signal.

Since conventional neural networks are static pattern classifiers, the EEG signal must be segmented into "iframes" during which the signal properties can be deemed to be stationary. The EEG is usually considered to be quasi-stationary over intervals of the order of one second, as this is the characteristic time of key transient features such as sleep spindles. The important information in the EEG is in the frequency domain. An auto-regressive (AR) model of the EEG signal provides adequate representation of the EEG during the sleep-wake continuum and may be used as an input representation to train and test the neural network. If a 10 coefficient model is used, for example, this gives a 10-dimensional input vector to the neural network for every one-second segment of EEG. In the case of vigilance monitoring the optimal number of coefficients is typically higher than 10, as the signal becomes more complex during wakefulness so that a higher order model is needed to describe it fully.

The signal from a novel electrode site such as the mastoid site cannot be easily analyzed using the standard human scoring methods discussed above.

According to a fourth aspect of the present invention there is provided a method of training and testing a first neural network for use in a physiological monitor, the method comprising;

(1) obtaining a first set of physiological signals from a subject, each member of the set being obtained over a period of epochs on a subject;

(2) obtaining a second set of physiological signals from the subject, each member of the set being obtained over the same epochs as a respective member of the first set of signals, and having a correlation with the respective member of the first set of signals;

(3) assigning a class to each epoch by analysing the set of first signals by a known method;

(4) separating each set of signals into a set of training signals and a set of test signals;

(5) training a second neural network by inputting the training set of first signals and using the classes assigned to each epoch as training labels;

(6) training the first neural network by inputting the training set of second signals and using the classes assigned to respective epochs of the first set of signals as the training labels; and (7) monitoring the performance of the first neural network by comparing the class assigned to each epoch by the first and second networks when input with the second and first set of test signals.

The fourth aspect of the present invention provides a method of training a neural network to act on input data (ie the second signals) which cannot be analyzed in a conventional way. Provided that there is a correlation (which may be non-linear) between the two sets of signals, the first neural network can be trained using the second signals as input data, but using labels which are obtained from the first signals in a conventional way.

For example, the signals may be derived from different physiological measurements; for example, the first set of signals may comprise signals derived from the EEG of a subject, and the second set of signals may relate to the blood pressure of the subject over simultaneous epochs.

Preferably however the method is used to train and test the neural network of a sleep or vigilance monitor which is used to monitor an electrical signal (ie. the second electrical signal) which cannot be analyzed using standard polysomnography analysis. The second network is trained using labels obtained from a first set of signals from standard sites (typically EEG from the scalp, two EOG signals and an EMG signal) which can be analyzed using standard polysomnography analysis. Typically the second electrical signal is an EEG signal obtained from an electrode site which cannot necessarily be scored by humans (such as the mastoid site).

The technique of training a neural network to obtain the same output from indirectly related but different input signals (in this case, of EEG taken from different sites) can equally be applied to other analysis systems including an off-line sleep or vigilance analysis system that retrospectively analyses stored data.

According to a fifth aspect of the present invention there is provided a method of assigning a class to an epoch of a physiological signal obtained from a subject as a set of samples, the method comprising (1) estimating the probability of each of a plurality of stage types for each sample;

(2) cumulatively multiplying the probabilities for each sample with the probabilities of a previous sample;

(3) determining which stage type has the highest probability when all samples in the epoch have been cumulatively multiplied; and (4) assigning that stage type to the epoch.

Typically the physiological signal comprises an EEG signal. The signal may be obtained from the mastoid site.

Preferably the methods of the fourth and/or fifth aspects of the invention are employed in the production and/or operation of an insomnia monitor according to the first aspect of the invention or a vigilance monitor according to the second aspect of the invention. In addition, the methods of the fourth and/or fifth aspects of the present invention may be combined with a method according to the third aspect of the present invention.

BRIEF DESCRIPTION OF THE DRAWINGS

Embodiments of all aspects of the present invention will now be described with reference to the accompanying drawings, in which:

FIG. 4 is an example of the neural network's outputs;

FIG. 8 illustrates the Kohonen maps from independent analysis made on data recorded simultaneously from standard and novel EEG electrode sites; and, FIGS. 9(a)–9(f) illustrate conventional EEG traces for the various stages of sleep.

EMBODIMENT

Figure 1:
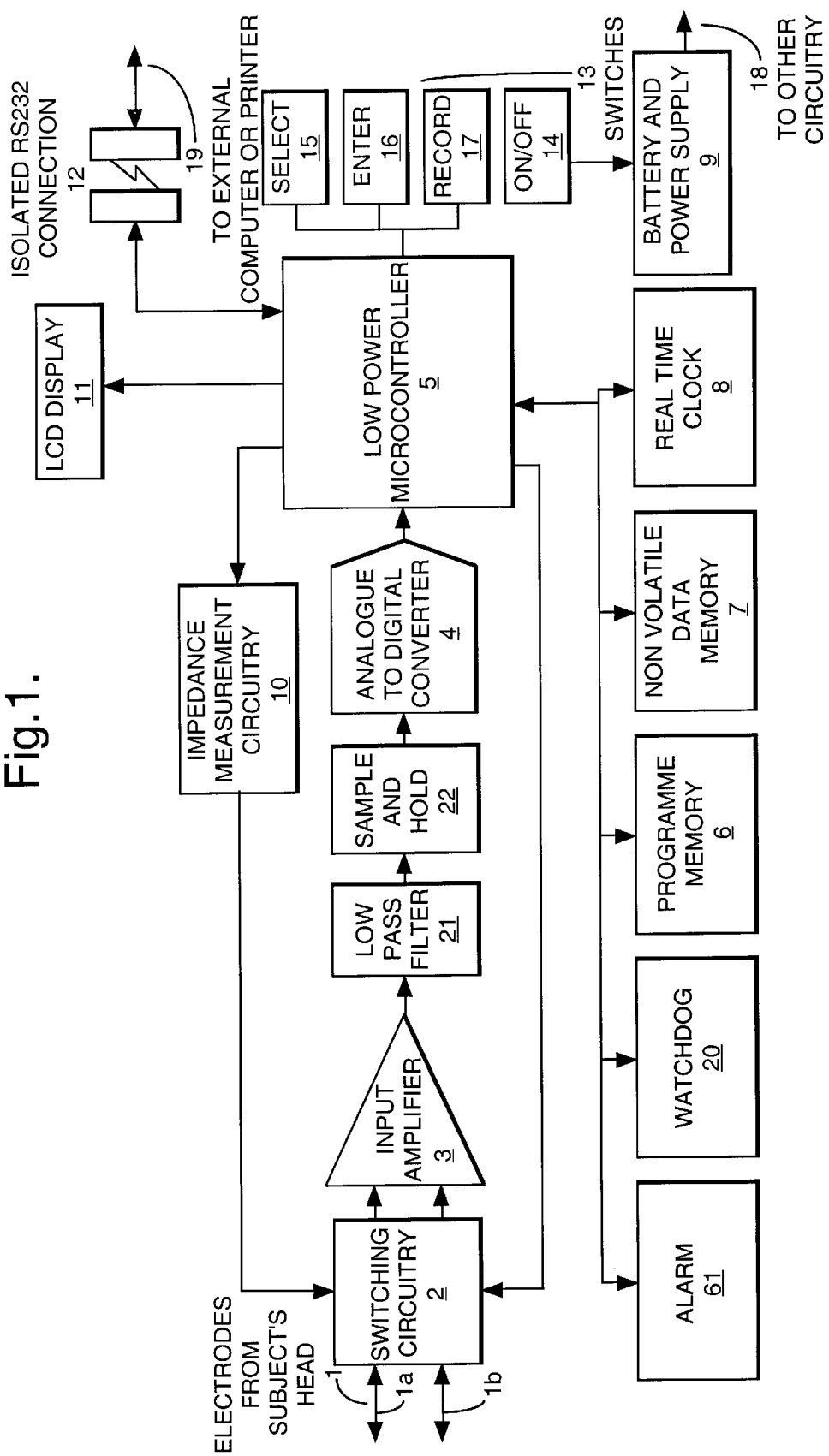
FIG. 1 is a block diagram of an embodiment of an insomnia monitor or vigilance monitor according to the first and/or second and fifth aspects of the present invention.

A block diagram of a typical implementation of the device according to the invention is described below, which refers to FIG. 1.

The device is a small, self contained portable unit that can continually acquire and analyze EEG signals for at least 12 hours. Results are held in non-volatile data memory 7 for later display on LCD display 11 or down-loading via an isolated RS232 link 12.

Power is provided by internal primary or rechargeable batteries and a regulated power supply 9.

Signals are acquired from electrodes 1 mounted on the subject's head via switching circuitry 2 and input amplifier 3. The input amplifier has an analogue bandwidth of at least 0.5Hz–30Hz and is of a high gain, low noise instrumentation design. The signal is input to low-pass filter 21 to reduce unwanted aliasing components before analogue to digital conversion. The signal is regularly held by sample and hold circuit 22 and converted to digital format by analogue to digital converter 4. The resultant quantised data samples are transferred to low power microcontroller 5 for processing. The sampling rate is typically 128Hz and the quantisation of the analogue to digital converter 4 is typically 12 bits, which provides sufficient dynamic range not to require a gain control on the input amplifier 3.

When recording one channel of EEG from the mastoid site, three electrodes are typically necessary; two of them (1a,1b) comprise the differential inputs to input amplifier 3 (the recording is of one part of the body with respect to another; in this case the two parts are the two mastoid sites), and the third is an "indifferent" lead (not shown) whose sole function is to allow input amplifier return currents to flow. The indifferent lead can be attached to any part of the subject's body. It is possible to produce an amplifier without an indifferent lead, but the performance is not as satisfactory. Due to the low amplitude of the signals (in the 0–200 $\mu$V range), the fact that the subject is fairly mobile, and the uncontrolled environment in which the equipment is operating, the number of potential sources of artefact contamination of the signal are substantial; a poorly designed system will even detect the passage of the subject through the earth's magnetic field.

Before signal acquisition begins, the impedances of the electrodes on the subject's head are measured by causing impedance measurement circuitry 10 to drive a signal of known amplitude and source impedance via the switching circuitry 2 through each of the electrodes 1a, 1b in turn onto the subject's scalp. The resultant signal is measured by the microcontroller by the process described above and from it the impedances of each of the electrodes fitted to the subject's scalp are calculated in turn. A warning message is displayed on the LCD display 11 if the impedance of either of the connections to the subject's head is unacceptably high.

During data acquisition, the device continually acquires EEG signals from the subject's head for analysis. The microcontroller 5 analyses the quantised values and from them generates results that are stored in the non-volatile data memory 7.

The programme for the microcontroller is held in programme memory 6.

Real-time clock 8 which can be read from and written to by the microcontroller 5 allows the results to be stored relative to the time of day.

Watchdog 20 resets the microcontroller 5 if the microcontroller fails to write to it periodically. If the microcontroller 5 is reset it will identify whether it was in record before the reset was received and if so, go back into record so that a minimal amount of data is lost.

Alarm 61 may be activated if the device is a vigilance monitor and the processor 5 has determined that the level of vigilance of the subject is unacceptably low.

Control of the device is via switches 13, some of which can be read by the microcontroller 5. On/Off switch 14 turns the device on and off; select switch 15 displays successive prompts and results on the LCD screen 11; enter switch 16 accepts the command currently displayed on the LCD screen 11; record switch 17 puts the device into record which starts signal acquisition, processing and storage.

When the device is switched on the user can choose whether to view the results from the previous recording; down-load the results from the previous recording into a computer or to a printer; delete the results from the previous recording; or go into record, after first performing an automatic impedance measurement.

The neural network is a software algorithm running on the microcontroller 5. It could be implemented directly in hardware to reduce power consumption.

The low pass filter 21 can be either part of the input amplifier 3 or be achieved in the sampling process itself within the analogue to digital converter 4 if a sigma-delta device is employed.

The index can be displayed on an LCD display, an LED display, or all control and output information can be displayed on an external computer 19 (e.g. via an RS232 connection).

The RS232 connection 12 can be any type of communications interface to another piece of equipment, with or without a built-in isolation barrier, or it can be omitted entirely.

There may not need to be a power supply circuit 9, the device using the output of the batteries directly.

The alarm 61 may be replaced by a software transmission to an external piece of equipment such as external computer 19 via R5232 connection 12.

There need not be the controls illustrated. All that is necessary is to start the recording, stop the recording and display the results.

The stored results can include or exclude the original EEG; the second-by-second neural network outputs; the individual epoch stage classifications.

Impedance measurement could be started manually or automatically or be omitted entirely if alternative means of measurement were available.

Figure 2:
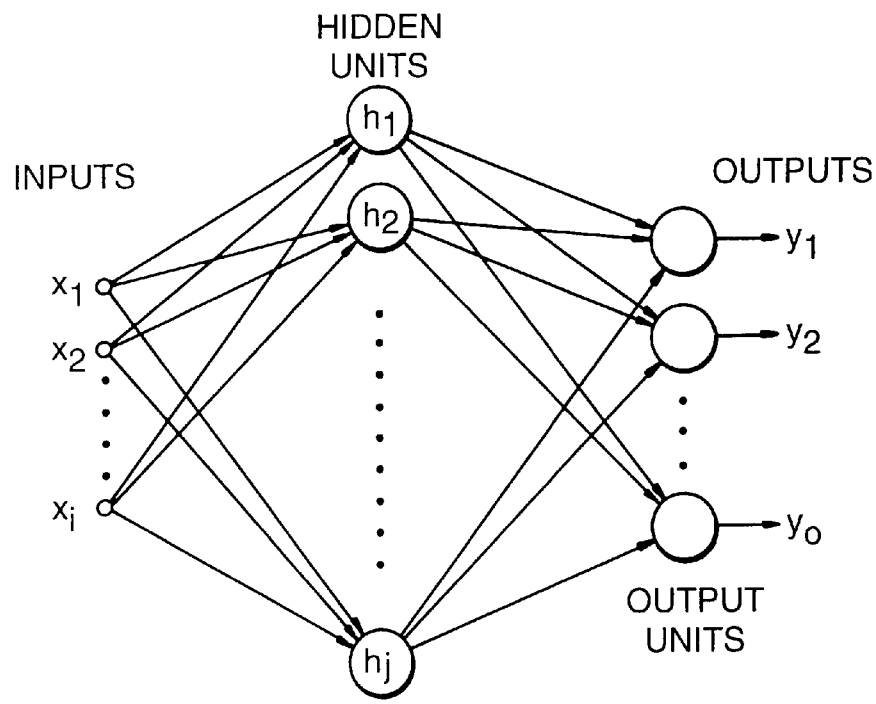
FIG. 2 illustrates an example of the multi-layer perceptron (MLP) neural network used by the monitor.
Figure 3:
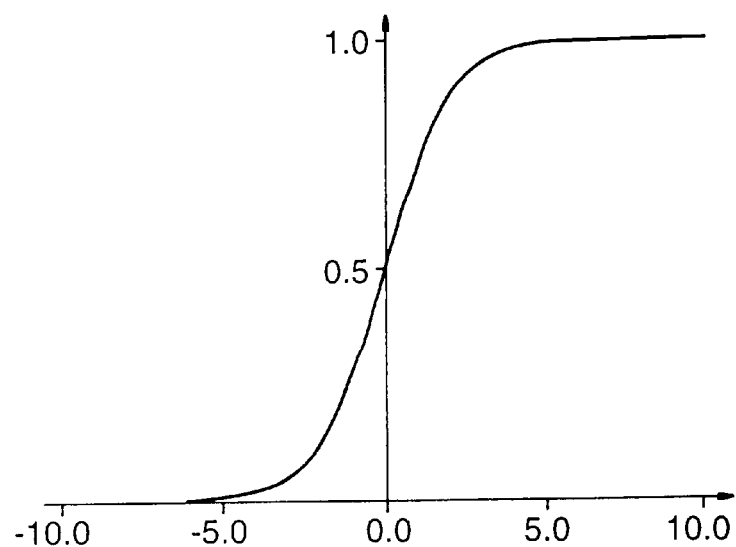
FIG. 3 illustrates the sigmoidal non-linearity used in each of the MLP's hidden and output units.

An example of the MLP architecture implemented in the microcontroller 5 is shown in FIG. 2. This comprises a number of inputs $x_1, x_2, \ldots x_i$, a number of units $h_1, h_2, \ldots h_j$ in a so-called hidden layer, and a number of output units $y_1, y_2, \ldots y_o$ with weighted connections linking each input to the hidden units and the hidden units to the output units. The input to each unit is a weighted sum of the outputs from the units in the preceding layer (or the inputs to the network in the case of the hidden units). The output from each unit is a nonlinear function of the weighted sum at its input. The non-linearity used in each unit is usually a sigmoidal function of the form shown in FIG. 3, so that the response of each unit to the weighted sum at its input is always bounded between 0 and 1.

The neural network thus performs a nonlinear mapping from its inputs to its outputs, with the form of this mapping determined by the values of its connection weights. These weights have random values to begin with, but are then adapted during a subsequent training phase by presenting the vectors at the network's inputs for which the target classification (e.g. W,REM/S1 or S4) at the network's outputs is already known (labelled data). The values of the connection weights are then iteratively adjusted so that the observed response at the network's outputs more closely resembles the desired response.

The most popular training algorithm for MLPs is the error back-propagation algorithm. This seeks the set of weights which minimises the mean of the squared errors between the network's observed outputs and the corresponding desired outputs over all of the input vectors in the training set of labelled data. If the latter contains N input vectors then the error criterion to be minimised is given by:

$$E = \frac{1}{N} \sum_{i=n}^{N} \left[ \sum_{k=1}^{K} (y_{kn} - d_{kn})^2 \right] \quad (1)$$

where K is the number of network outputs; $Y_{1n}, Y_{2n}, \ldots, Y_{Kn}$ is the response at these outputs to the nth input vector in the training set and $d_1n, d_2n, \ldots, d_{Kn}$ are the desired output values.

The vectors generated for one-second sections of consensus-scored data are divided into a training set and a test set. If three processes (Wake, REM/stage 1 and slow wave sleep) are to be separated, then the desired output values used during training are [1,0,0] for Wakefulness, [0,1,0] for REM/stage 1 and [0,0,1] for Deep Sleep. To separate these three processes the performance on the test set is optimal when six hidden units are used (i.e. the MLP has a 10-6-3 architecture).

If the classes have overlapping distributions in feature space, then the output values obtained for input vectors in the overlap regions will be somewhere between 0 and 1. It has been shown (a well-known result in the literature) that these output values can be interpreted as probability estimates. Hence they represent the probabilities that an input vector belongs to one of the three output classes. This enables the MLP to interpolate between these classes when input vectors from sections of intermediate sleep are subsequently presented to it. This means that the MLP, trained exclusively on input vectors for Wakefulness, REM/stage 1 and stage 4, for instance, can track the entire sleep-wakefulness continuum.

The results in FIG. 4(a)–(c) show the time course of the network's outputs when the tenth-order AR model is fitted to each second of a 7¼-hour EEG sleep recording. These reveal all of the key features of a normal night's sleep, starting in FIG. 4(a) and (c) with a rapid descent from wakefulness to deep sleep, and followed in FIG. 4(b) and (c) by a regular cycling of REM and Deep Sleep as sleep waxes and wanes through the night. The mean values of the outputs in FIG. 4(b) and (c) increase and decrease respectively as the night progresses, reflecting the predominance of deep sleep early in the night, followed by an increase in the amount of REM sleep in later cycles.

Figure 5:
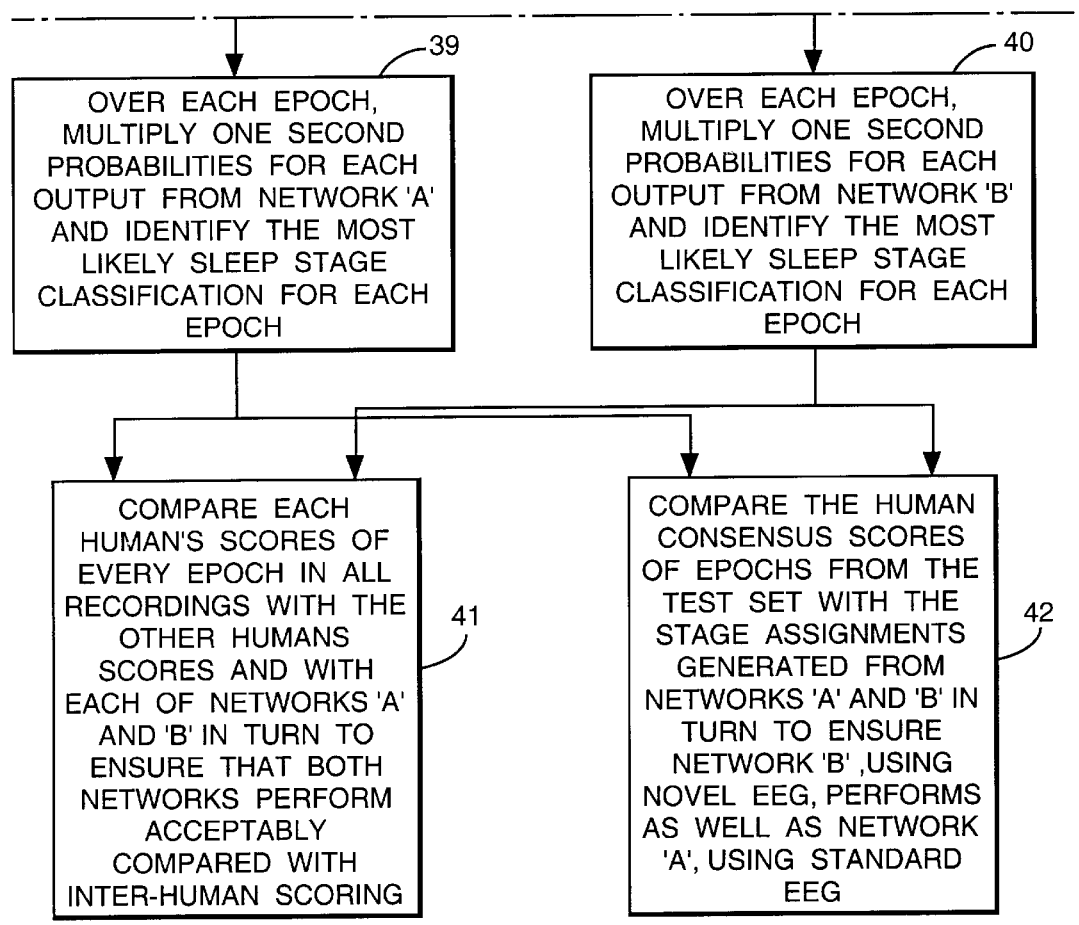
FIG. 5 is a block diagram illustrating an embodiment of the method of training and testing the neural network according to the fourth aspect of the present invention.
Figure 6A:
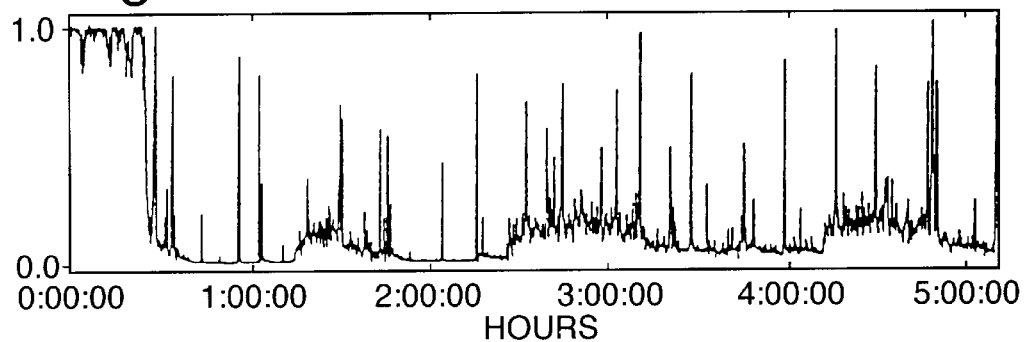
FIGS. 6(a) to 6(c) illustrate second-by-second output probabilities from a three-class MLP for (a) Wakefulness, (b) Light Sleep/REM, (c) Deep Sleep.
Figure 6B:
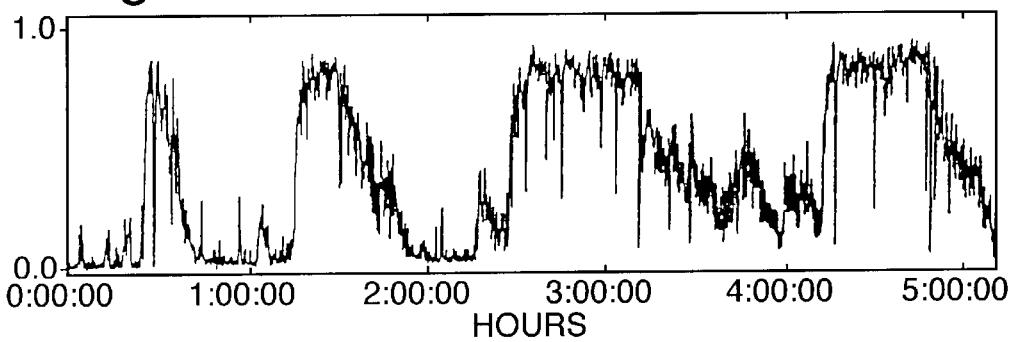
Figure 6C:
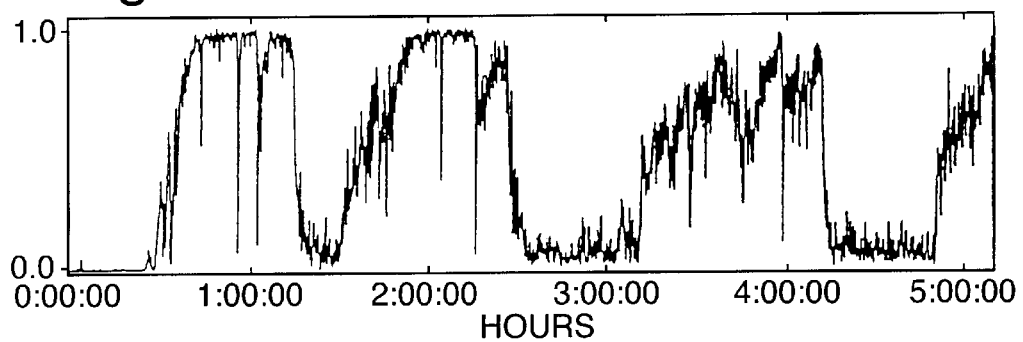
Figure 6D:
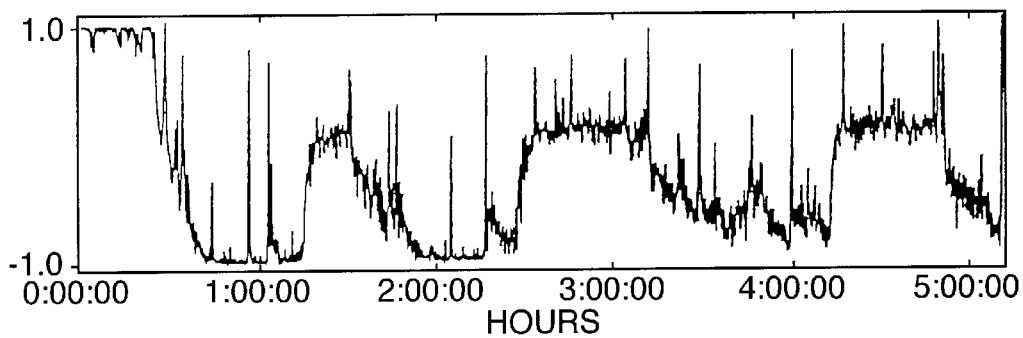
FIG. 6(d) illustrates the pseudo-hypnogram obtained by subtracting (c) from (a)
Figure 6E:
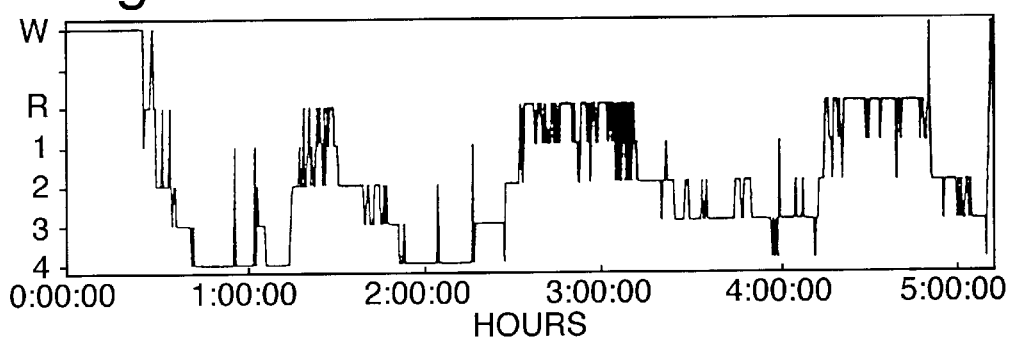
FIG. 6(e) illustrates a hypnogram obtained by multiplying output probabilities according to the fourth aspect of the invention from a six-class MLP over 30-second epochs.
Figure 6F:
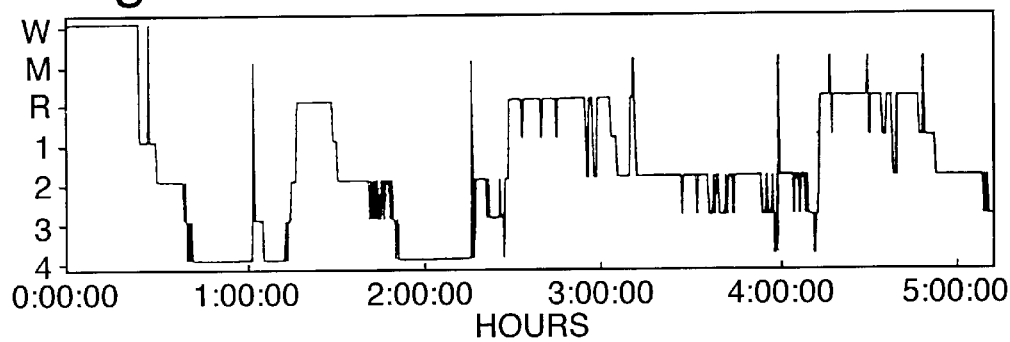
FIG. 6(f) illustrates the corresponding human/scored hypnogram.

A flow chart illustrating a method according to the fourth aspect of the present invention used to develop algorithms capable of scoring sleep or determining the level of vigilance from novel electrode sites is shown in FIG. 5. Unless otherwise stated the descriptions that follow apply to an insomnia monitor but identical principles of operation also apply to a vigilance monitor.

Recordings are made on several subjects, simultaneously recording signals 30 from standard sites for EEG, EOG (×2) and EMG, and from the novel site. The novel site chosen may typically be the mastoid site behind the ear.

Each recording is scored by at least 3 human experts at 31, who score each epoch in the recording according to pre-agreed rules. These may typically be the rules of Rechtschaffen and Kales. The standard electrode position must be used because no rules exist for scoring from other electrode sites.

Those epochs for which there is consensus agreement of scores are identified at 32 and randomly divided at 33 into a training set, the EEG from which will be used to train the neural network, and a test set against which the network's performance will be measured. The same number of epochs for each stage type must be included in the training set to ensure a balanced representation of the signal within the network.

All the recordings are divided into short windows (one second has been found to be optimal and will be assumed for the rest of this description) and each window is preprocessed using a frequency domain representation to identify the dominant frequencies within it. An all-pole, autoregressive model and a Kalman filter have both been shown to work effectively as preprocessors. For each window, the coefficients of the filter provide a representation of the dominant frequencies in the EEG present within it and are used as inputs to the neural network. The standard and novel EEG channels are filtered separately at 34.

Two neural networks are trained. Network "AA" is trained at 35 on filter coefficients from preprocessed standard EEG, and network "B" is trained at 36 on filter coefficients from preprocessed novel EEG. The training labels for both networks are the consensus human scores. Only data from the training epochs are used. The outputs from training are connection weights for the two neural networks.

It has been shown that the sleep wake continuum can be fully described in terms of three continuous processes, corresponding to human scored stages Wake, REM/Stage 1 and stage 4. These stages are therefore the minimum stage classifications that must be part of the training set and result in a neural network that generates three outputs, corresponding to the probabilities that the subject is in Stage Wake, Stage REM/Stage 1 and Stage 4 (using the preprocessed EEG signal alone as input, the network is unable to discriminate between human scored Stage REM and stage 1 sleep, but the distinction is unnecessary for vigilance or insomnia studies). The performance of the network is measured by the error rate classification when the network is fed with data from the test set.

Each recording in turn is then analyzed at 37 using network "A". For each recording three probabilities are generated per second. The complete recordings are processed. Coefficients from the preprocessor fed with EEG from the standard electrodes site are used as inputs 37.

Each recording in turn is then analyzed using network "B" in the same way, using coefficients from the preprocessor fed with novel EEG 38.

A method of assigning a class to an epoch according to the fifth aspect of the present invention is implemented in the device of FIG. 1 and is described below with reference to FIGS. 6 and 7. Compared with the epoch length (typically 20–40 secs), the network outputs are over-sampled. A single sleep stage classification is required for the whole epoch, derived from the one-second network outputs. The following method is used to convert from 20, 30 or 40 sets of three probabilities to a single optimal classification for the epoch.

The mean 3-D vector over an epoch, for each of the chosen classes (typically Wake, REM/Stage 1, Stages 2, 3 and 4), for all the data in the training set, is first determined. For each of the one-second probability outputs from the analyzed recordings, the successive probabilities are multiplied together over each epoch to generate a 3-D vector for that epoch. A nearest class mean classification method is used to assign a state to the vector describing that epoch.

This is described in more detail below.

Since the MLP employs a one-out-of-N output coding and is trained by minimising a squared error cost function, the outputs are estimates of posterior probabilities which can be combined probabilistically over time to give a classification over, say, 30-second epochs.

Assuming that the successive input vectors form an independent sample set (an assumption, of course, which is not entirely valid), combined output probabilities can be computed by multiplying individual outputs:

$$[P_k]_{comb} = \prod_{m=1}^{M} [y_{km}] \qquad (2)$$

where $[P_k]_{comb}$ is the kth combined output probability, and $[y_{km}]$ is the kth output from the mth observation. (For a 3-output network, $1 \leq k \leq 3$; for 30-second epochs, M =30.)

In order to make sure that negative and near zero outputs are not generated, a softmax function is used during both training and testing. The softmax function is:

$$\text{softmax}(y_k) = \frac{\exp(y_k)}{\sum_k \exp(y_k)} \qquad (3)$$

Using the softmax function ensures that individual outputs are always between 0 and 1, and that outputs sum to one. Corresponding outputs from successive segments can be multiplied together (alternatively the logarithms of the probability values can be added together). The index of the maximum combined probability determines the classification.

The objective of the probabilistic combination described above is, of course, to generate hypnograms for complete epochs of the chosen duration (eg 30 seconds), with the same output classifications as the selected rule system. Since it is not possible, however, to discriminate between human-scored stage REM and stage 1 sleep on the basis of the EEG alone, the neural network can only be used to generate in the case of an insomnia monitor a 5-state classification (Wake, REM/stage 1, stage 2, stage 3 or stage 4). These 5 outputs can be generated, over the complete epochs, from a 3-output MLP of the type which has already been described or from a 5-output MLP. The training of the latter is similar to the training of the 3-output MLP, except that consensus-scored data for stage 2 and stage 3 are also used in the training phase.

If a three-output MLP is used, the mean 3-D vector over an epoch for each of the five classes is first determined from all the data in the training set. For each of the 30 one-second EEG segments belonging to a consensus- scored epoch of stage wake, stage REM/stage 1, stage 2, stage 3 or stage 4 sleep, the successive probabilities are multiplied together to generate a 3-D vector for that class. All such vectors are then averaged across the training data set to generate the mean vector for each of the 5 classes. Then, for each of the one-second probability outputs from the analyzed recordings, the successive probabilities are multiplied together over each epoch to generate the average 3-D vector for that epoch. A nearest class mean classification method is used to assign one of the 5 classes to the average 3-D vector describing that epoch.

If a five-output MLP is used, a simpler procedure is sufficient. For each of the one-second probability outputs from the analyzed recordings, the successive probabilities are multiplied together over each epoch to generate a 5-D vector for that epoch. The output with the largest resultant value is used to indicate the classification of that epoch.

The output is therefore two hypnograms for each recording, generated from the neural networks at 39,40 in FIG. 5.

A five way comparison is made between the hypnograms scored by each human and the hypnograms from the two neural networks to generate an inter-scorer rating for each stage type. The scoring of network "B" using novel EEG is compared with the scoring of network "A" using standard EEG, and each is compared with humans scoring against each other at 41.

The stage scores from the consensus scored epochs from the test data set are compared with the scores from network "A" and network "B", in turn. This allows the performance of the two networks to be compared on a data set that was not included in the original training set at 42.

FIG. 6 illustrates MLP outputs 6(a)–(c) and a hypnogram 6(e) obtained as described above. FIG. 6(f) shows the corresponding human-scored hypnogram.

Different types of neural network may be used. Results are similar using either a multi-layer perceptron (MLP) or a radial basis function (RBF) network.

The EEG signals from the preferred novel electrode site on the mastoid are generally more contaminated by noise than those from the standard (central) electrode site. It is important to ensure that the network is trained only using the highest quality data as its output is only as good as its training data. To ensure this, network "B" can be trained with data from just those sections of epochs from the training set for which network "A" agreed with the consensus classification with a reasonable probability.

Figure 7:
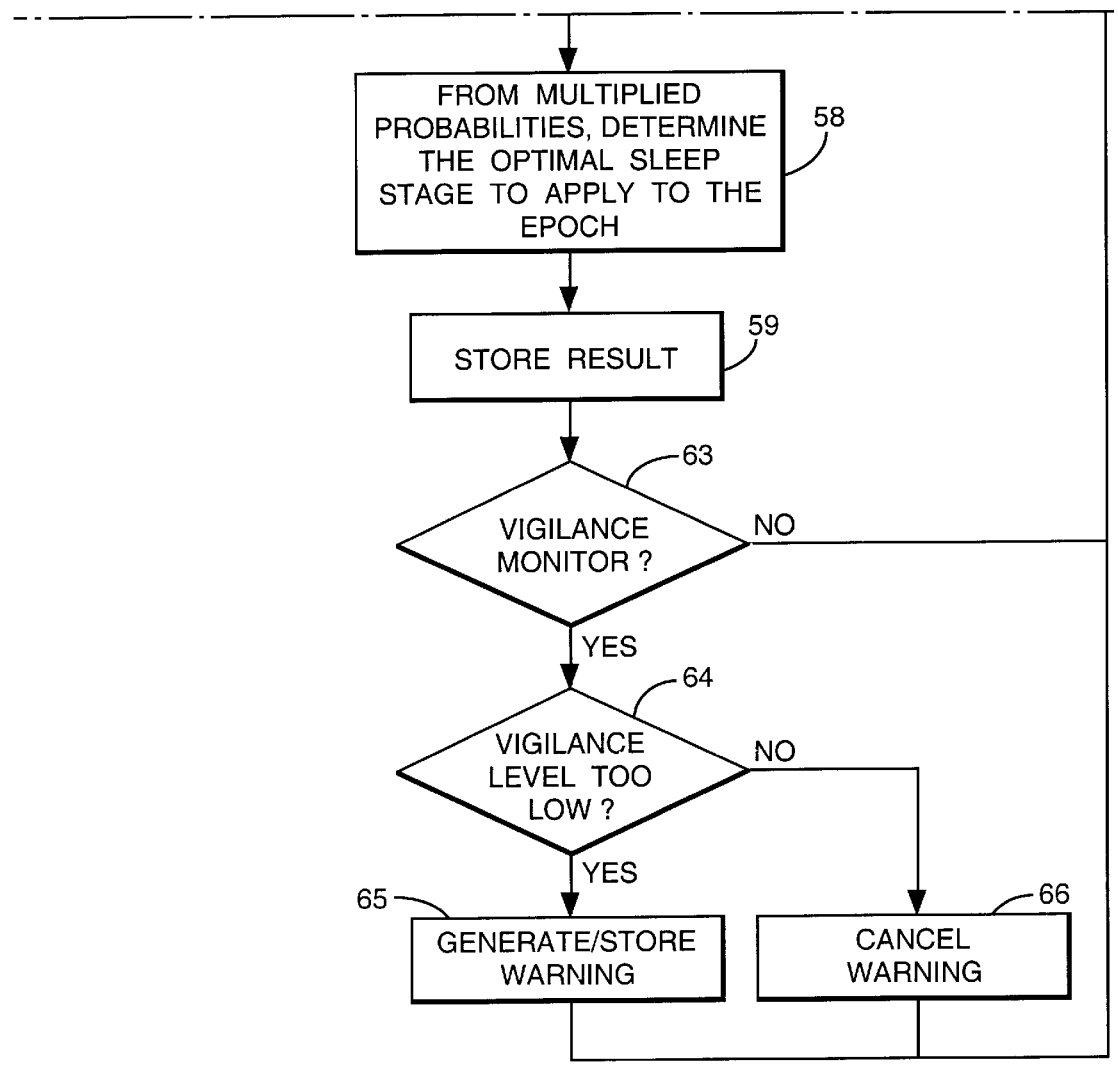
FIG. 7 illustrates the insomnia or vigilance monitor main processing loop.

A flow chart for the acquisition and processing of data according to the fourth aspect of the invention is shown in FIG. 7.

Once put into record 50, after checking whether the recording must continue 51 the microcontroller acquires data from the novel electrode site at 52 until it has a second's worth at 53. The data is preprocessed at 54 with the same preprocessor and 3 or 5 output neural network at 55 as used during the testing phase described above for network "B". Once an epoch's worth of data has been processed at 56, it is assigned a sleep stage at 57,58, again using one of the two methods described above for either a 3-output or 5-output network. The value is stored at 59 in non-volatile memory and the process continues until the end of the recording.

In the case of an insomnia monitor standard sleep statistics are generated at 60 from the resultant hypnogram, in particular, the sleep efficiency index, which is the ratio of the number of sleeping stages to total stages during the night. This figure is displayed to the subject or physician on request and is used to determine whether or not the subject had a good night's sleep. Alternatively or in addition the ratio of deep sleep (stage 3 or 4) to total time may be calculated and displayed. Alternatively or in addition the "quality" of deep sleep may be calculated by determining the length of each deep sleep episode, and displayed as a sleep "quality" index.

The device provides a summary of sleep using a low-cost device. No clinical expertise in sleep scoring is required to interpret the results. Electrode application is simple, using stick-on electrodes that are fitted below the hairline. No training is required to fit them.

Only three electrodes are required (two mastoid plus one indifferent electrode attached to any part of the body and to 0 V on the recorder via a suitable resistor) instead of between 7 and 9 for a standard polysomnographic recording (two EEG (in the hair), two or four for EOGs, two for EMG and an indifferent).

Standard summary analysis results are generated despite using an unconventional electrode site.

The unnecessary usage of hypnotic drugs is reduced by measuring objectively the quality of sleep.

In the case of a vigilance monitor, the vigilance level is monitored at 64, and if it drops below a predetermined threshold, a warning message is generated at 65. This may be used to alarm the subject, or may be stored for later analysis.

An experiment investigating the use of a mastoid signal is discussed below with reference to FIGS. 8A–H.

Figure 9A:
Figure 9B:
Figure 9C:
Figure 9D:
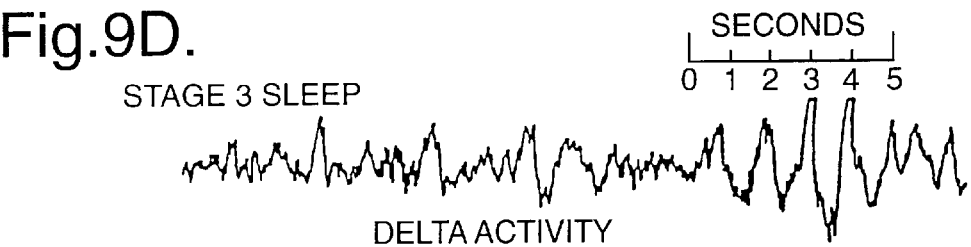

A set of overnight recordings was taken from ten subjects, consisting of a central EEG signal and two channels of mastoid EEG. The central EEG signal from each subject was scored by three experts. A balanced data set of central EEG data from all of the ten subjects was then constructed. The least well represented class was slow wave sleep: there were only 147 epochs (ie. 4410 seconds) of consensus-scored stage 3 and stage 4. The overall size of the database was therefore 4*4410 sets of 10-dimensional auto-regressive (AR) coefficients (one for each of the four classes: slow wave sleep—stage 3/stage 4, stage 2, REM/stage 1 and wakefulness). FIGS. 8A–D are 10*10 feature Kohonen maps for the central EEG data. Kohonen maps are a form of neural network which enable the visualisation of the 10-dimensional data. FIG. 9A corresponds with the wakefulness stage, FIG. 9B corresponds with the REM stage, FIG. 9C corresponds with the slow wave sleep stage and FIG. 9D corresponds with stage 2. The crosses on each map indicate the units which are most often visited by a given sleep stage. These maps provide a 2D visualisation of the 10-dimensional AR coefficients and their topological preservation properties allow us to verify whether stage 2 is an intermediate stage between REM/light sleep and deep sleep, for example. If we examine FIGS. 9A–C we see that wakefulness lies broadly in the lower part of the map, REM directly above it and slow wave sleep at the top of the map. Stage 2 is indeed an intermediate state as it is found in the middle of the map and at the top on the right hand side.

The corresponding mastoid EEG signals were extracted for the same 4*4410 one second segments and given the same labels as had been assigned to the central EEG data.

Figure 9E:
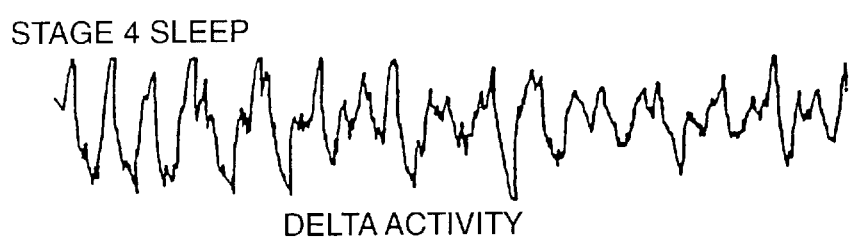
Figure 9F:

FIGS. 9E–H are 10*10 feature Kohonen maps for the mastoid EEG data. FIG. 9E corresponds with the wakefulness stage, FIG. 9F corresponds with the REM stage, FIG. 9G corresponds with the slow wave sleep stage and FIG. 9H corresponds with stage 2.

It is important to note that the central EEG maps (FIGS. 8A–D) and the mastoid EEG maps (FIGS. 8E–H) were independently trained, a fact which can be verified by the presence of a 90 degree rotation between FIGS. 8A–D and 8E–H. Taking this 90 degree rotation into account, it can be seen that the corresponding mastoid EEG data is very similar. This indicates that there is sufficient information in the mastoid EEG for discrimination between the four main types of sleep and also that this information can be extracted through the use of an auto-regressive model.

The methods and apparatus described previously may also be applied to apparatus for vigilance monitoring. That is, the insomnia monitor illustrated in FIG. 1 and trained according to the algorithm illustrated in FIG. 5 may be adapted as a vigilance monitor which is of particular use in safety-critical jobs. vigilance analysis requires segmentation and classification of an EEG signal during wakefulness as well as during sleep. The result of a vigilance analysis is a "Wakeogram". The scoring technique required for a Wakeogram is similar to that of a hypnogram, except that it encompasses states of wakefulness, as well as sleep. The two charts can be regarded as overlapping in light sleep. As with a hypnogram, the Wakeogram is scored according to rules based upon human observation of the EEG, EOG and EMG signals. The rules typically refer to the amount of time in each epoch that frequencies over specific band widths occur.

An example of a suitable Wakeogram scoring technique is described in "Acute effects of hydroxyzine on nocturnal sleep and sleep tendency: a C-EEG study" Alford C, Rombaught N, Jones J, Foley S, Idzikowski C, Hindmarch I; Human Psychopharmacology 1992 vol 7 pp 25–35.

The low power microcontroller 5 monitors the Wakeogram such that when the Wakeogram assigns an epoch to a category which indicates a high level of drowsiness, an alarm 61 is issued. This is typically an audible alarm. In addition, the vigilance monitor may store the Wakeogram and/or calculate and display a summary index of vigilance quality (for instance indicating the percentage time in which the subject is active and alert).

We claim:
1. A vigilance monitor comprising:
   (1) one or more electrodes for obtaining an electrical signal from a subject over a period of epochs, said electrical signal being related to a wakefulness stage type being experienced by said subject;
   (2) a processor adapted to analyze said electrical signal and assign one of a plurality of wakefulness stage types to each of said epochs to generate a Wakeogram;
   (3) means for monitoring said Wakeogram to determine whether said Wakeogram meets predetermined criteria; and
   (4) means responsive to said means for monitoring said Wakeogram to generate a message when said Wakeogram meets said predetermined criteria.

2. A vigilance monitor according to claim 1, wherein said electrical signal comprises a single electroencephalogram (EEG) channel, and said Wakeogram is generated from said electrical signal only.

3. A vigilance monitor according to claim 1, wherein said electrical signal is obtained from an electrode site which cannot necessarily be scored by humans.

4. A vigilance monitor according to claim 1, further comprising a memory adapted to store said Wakeogram.

5. A vigilance monitor according to claim 1, wherein said monitor comprises a single portable unit.

6. A vigilance monitor according to claim 1, wherein said processor comprises a neural network.

7. A method of training and testing a first neural network for use in a physiological monitor, the method comprising;
   (1) obtaining a first set of physiological signals from a subject, said first set being obtained over a first period of epochs on a subject;
   (2) obtaining a second set of physiological signals from said subject, said second set being obtained over said first period of epochs, and having a correlation with said first set of physiological signals;
   (3) assigning a class to each of said epochs by analyzing said first set of physiological signals by a known method;
   (4) separating said first set of physiological signals into a first set of training signals and a first set of test signals;
   (5) separating said second set of physiological signals into a second set of training signals and a second set of test signals;

(6) training a second neural network by inputting said first set of training signals and using said classes assigned to said epochs as training labels;

(7) training said first neural network by inputting said second set of training signals and using said classes assigned to said epochs as training labels; and (8) monitoring said first neural network by comparing a class assigned to each of said epochs by said first and second neural networks when input with said second set of test signals and said first set of test signals to obtain an indication of performance.

8. A method according to claim 7, wherein said first and second sets of physiological signals comprise EEG signals.

9. A method of assigning a class to an epoch of a physiological signal obtained from a subject as a set of samples, the method comprising (1) estimating a probability of each of a plurality of stage types for each of said samples;

(2) cumulatively multiplying said probabilities for each of said samples with the probabilities of previous samples;

(3) determining which of said stage types has a higher probability than all other of said stage types when all of said samples in said epoch have been cumulatively multiplied; and (4) assigning said determined stage type to said epoch.

10. A method according to claim 9, wherein said physiological signal comprises an EEG signal.

11. A method of vigilance monitoring, the method comprising:

(1) obtaining an electrical signal from a subject over a period of epochs, said electrical signal being related to a wakefulness stage type being experienced by said subject;

(2) analyzing said electrical signal and assigning one of a plurality of wakefulness stage types to each of said epochs to generate a Wakeogram;

(3) monitoring said Wakeogram to determine whether said Wakeogram meets predetermined criteria; and (4) generating an alarm message when said Wakeogram meets the predetermined criteria.

12. A method according to claim 11, wherein said electrical signal comprises a single EEG channel, and said Wakeogram is generated from said single EEG channel only.

13. A method according to claim 11, wherein said analyzing of said electrical signal is performed using a neural network.

* * * * *